United States Patent
Nakamura et al.

(10) Patent No.: US 11,540,954 B2
(45) Date of Patent: Jan. 3, 2023

(54) ELASTIC COMPOSITE SHEET MANUFACTURING METHOD

(71) Applicant: ZUIKO CORPORATION, Settu (JP)

(72) Inventors: Hideyuki Nakamura, Settu (JP); Yukihiko Fujita, Settu (JP); Miwa Koshijima, Settu (JP)

(73) Assignee: ZUIKO CORPORATION, Settu (JP)

( * ) Notice: Subject to any disclaimer, the term of this patent is extended or adjusted under 35 U.S.C. 154(b) by 0 days.

(21) Appl. No.: 16/963,386

(22) PCT Filed: Dec. 17, 2018

(86) PCT No.: PCT/JP2018/046420
§ 371 (c)(1),
(2) Date: Jul. 20, 2020

(87) PCT Pub. No.: WO2019/150801
PCT Pub. Date: Aug. 8, 2019

(65) Prior Publication Data
US 2021/0161728 A1   Jun. 3, 2021

(30) Foreign Application Priority Data
Jan. 31, 2018   (JP) .............................. JP2018-014323

(51) Int. Cl.
*A61F 13/15*   (2006.01)
*B29C 48/00*   (2019.01)
(Continued)

(52) U.S. Cl.
CPC .................. *A61F 13/15804* (2013.01); *A61F 13/15707* (2013.01); *A61F 13/15764* (2013.01);
(Continued)

(58) Field of Classification Search
None
See application file for complete search history.

(56) References Cited

U.S. PATENT DOCUMENTS

| 5,681,302 A | 10/1997 | Melbye et al. |
| 6,291,039 B1 | 9/2001 | Combe et al. |

(Continued)

FOREIGN PATENT DOCUMENTS

| EP | 3747620 A1 | 12/2020 |
| EP | 3750704 A1 | 12/2020 |

(Continued)

OTHER PUBLICATIONS

PCT/ISA/210, "International Search Report for International Application No. PCT/JP2018/046420," dated Mar. 5, 2019.

(Continued)

*Primary Examiner* — Barbara J Musser
(74) *Attorney, Agent, or Firm* — Manabu Kanesaka (57) ABSTRACT

An elastic resin material having a thermoplastic elastic resin as a main component is heated and melted, and the elastic resin material is discharged in a film or a linear shape from a discharge mechanism to form a film-shape or a linear-shape intermediate product. At a temperature above the temperature region at which the elastic resin material elastically deforms, extending is performed until the thickness or width of the film-shape intermediate product or the thickness of the linear-shape intermediate product assumes a prescribed value; with a cooling roller, the intermediate product is cooled to the temperature region at which the elastic resin material elastically deforms, and the intermediate product is hardened, forming a film-shape or linear-shape elastic member. The elastic member is stretched with a stretch roller to a prescribed stretching ratio, and the stretched elastic member is laminated on and bonded to a first base material sheet.

6 Claims, 5 Drawing Sheets

(51) Int. Cl.
  *B29C 55/06* (2006.01)
  *B29L 31/48* (2006.01)
(52) U.S. Cl.
  CPC ...... *B29C 48/0018* (2019.02); *B29C 48/0021* (2019.02); *B29C 55/06* (2013.01); *A61F 2013/15878* (2013.01); *B29L 2031/4878* (2013.01)

(56) References Cited

U.S. PATENT DOCUMENTS

| | | | |
|---|---|---|---|
| 6,969,441 | B2 | 11/2005 | Welch et al. |
| 7,442,332 | B2* | 10/2008 | Cancio ............... B29C 48/90 264/209.5 |
| 2002/0002021 | A1* | 1/2002 | May ..................... B32B 5/26 442/329 |
| 2006/0083893 | A1 | 4/2006 | Ashraf |
| 2009/0017297 | A1* | 1/2009 | Amon ................ B29C 43/24 428/349 |
| 2017/0306536 | A1* | 10/2017 | Conrad ............... B32B 7/14 |
| 2021/0031428 | A1 | 2/2021 | Nakamura et al. |
| 2021/0038440 | A1 | 2/2021 | Koshijima et al. |

FOREIGN PATENT DOCUMENTS

| | | |
|---|---|---|
| JP | H10-501195 A | 2/1998 |
| JP | 3054930 B2 | 6/2000 |
| JP | 2000-211013 A | 8/2000 |
| JP | 2001-504899 A | 4/2001 |
| JP | 2001-346825 A | 12/2001 |
| JP | 2008-516805 A | 5/2008 |

OTHER PUBLICATIONS

Europe Patent Office, "Search Report for European Patent Application No. 18903945.6," dated Oct. 1, 2021.

* cited by examiner

ELASTIC COMPOSITE SHEET MANUFACTURING METHOD

TECHNICAL FIELD

The present invention relates to a manufacturing method and manufacturing device of an elastic composite sheet, for example, relates to a manufacturing method and manufacturing device of an elastic composite sheet suitably usable for a disposable wearing article.

BACKGROUND ART

Figure 8:
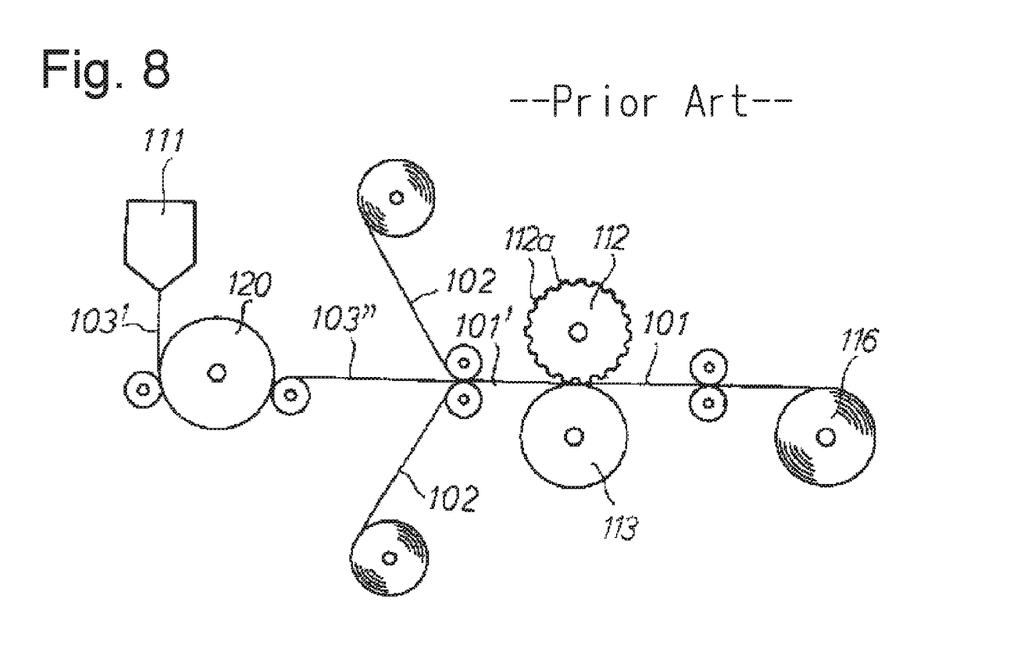
FIG. 8 is a schematic illustration showing the manufacturing method of the elastic composite sheet. (First conventional example)

An elastic composite sheet that is excellent in stretchability is used for the back sheet of a disposable diaper and the like. FIG. 8 is a schematic illustration showing a manufacturing method of the elastic composite sheet. As shown in FIG. 8, a thermoplastic elastic resin is extruded from a T die 111 to form a film-shape object 103' in a molten state. Then, the film-shape object 103' is cooled by a chill roller 120. Then, the cooled film-shape object 103" is sandwiched between two sheets of continuous nonwoven fabric 102 and at the same time, embossing is performed thereon. The embossing is performed by pressurization and nipping with an embossing roller 112 having a multiplicity of dot-shape convex portions 112a formed on the surface thereof and a backup roller 113. An elastic composite sheet 101 in which the layers are bonded and integrated by the embossing is wounded by a winding roller 116. As the nonwoven fabric 102, a nonwoven fabric is used that is stretchable at least in a lateral direction (a direction vertical to the flow direction and the thickness direction of the nonwoven fabric 102) (for example, see Patent Literature 1).

CITATION LIST

Patent Literature

[Patent Literature 1] Japanese Patent No. 3054930

SUMMARY OF THE INVENTION

Problem to be Solved by the Invention

For example, when an elastic composite sheet is used for a disposable diaper, characteristics required for the elastic composite sheet such as the stretching stress, the expansion and contraction ratio, the texture and the air permeability vary according to the part where it is used and the product type.

However, with the conventional elastic composite sheet manufacturing device, the characteristics of the elastic composite sheet that it can manufacture are limited and it is difficult to manufacture an elastic composite sheet having desired characteristics.

In view of such circumstances, a problem to be solved by the present invention is to provide a manufacturing method and manufacturing device of an elastic composite sheet capable of easily manufacturing an elastic composite sheet having desired characteristics.

Means for Solving the Problem

To solve the above-mentioned problem, the present invention provides an elastic composite sheet manufacturing method structured as follows:

The elastic composite sheet manufacturing method is provided with: (i) a first step of heating and melting an elastic resin material having a thermoplastic elastic resin as a main component; (ii) a second step of forming a film-shape or a linear-shape intermediate product by discharging the melted elastic resin material in a film or a linear shape; (iii) a third step of extending the intermediate product at a temperature higher than a temperature region at which the elastic resin material elastically deforms, until the thickness or width of the film-shape intermediate product or the thickness of the linear-shape intermediate product assumes a prescribed value; (iv) a fourth step of forming a film-shape or a linear-shape elastic member by cooling the intermediate product to the temperature region at which the elastic resin material elastically deforms and hardening the intermediate product; (v) a fifth step of stretching the elastic member to a prescribed stretching ratio; and (vi) a sixth step of laminating the stretched elastic member on the first base material sheet and bonding the elastic member to the first base material sheet.

By the above-described method, an elastic composite sheet can be manufactured in which the elastic member and the first base material sheet are bonded to each other.

According to the above-described method, an elastic composite sheet having desired characteristics such as desired stretching stress can be easily manufactured with equipment having a simple structure, and furthermore, the manufacturing cost can be reduced.

Preferably, at the sixth step, the second base material sheet is superposed on the elastic member and the first base material sheet in such a manner that the elastic member is sandwiched between the first base material sheet and the second base material sheet, (a) the second base material sheet is bonded to at least one of the stretched elastic member and the first base material sheet, or (b) the second base material sheet is bonded to the first base material sheet, the elastic member is not bonded to the first base material sheet or the second base material sheet and only by friction between the first base material sheet and the second base material sheet, the elastic member is held between the first base material sheet and the second base material sheet.

"Only by friction between the first base material sheet and the second base material sheet, the elastic member is held between the first base material sheet and the second base material sheet" refers to, specifically, a condition or the like in which, for example, when the base material sheets are bonded to each other on both sides in the width direction of the elastic member in a stretched state and at an interval narrower than the width of the elastic member in a relaxed state, the elastic member having become thick because of the relaxing is sandwiched between the base material sheets and by the frictional force caused between the elastic member and the base material sheets, the elastic member is sandwiched between the base material sheets.

In this case, an elastic composite sheet can be manufactured in which the elastic member is sandwiched between the first and second base material sheets.

Preferably, at the third step, the intermediate product is extended by periodically changing the prescribed value to which the intermediate product is extended.

In this case, an elastic composite sheet can be manufactured in which the coefficient of elasticity of the elastic member varies according to the position in the extension direction of the elastic member.

Preferably, at the fifth step, the elastic member is stretched while the prescribed stretching ratio to which the elastic member is stretched is periodically changed.

In this case, an elastic composite sheet can be manufactured in which the stretching rate of the elastic member varies according to the position in the stretching direction of the elastic member.

Preferably, at the third and fourth steps, by providing a plurality of cooling members having different temperature conditions so that the intermediate product passes the cooling members successively, the intermediate product is cooled in a plurality of steps.

In this case, the quality of the elastic member can be stabilized.

Preferably, at the third and fourth steps, a condition for cooling the intermediate product is made to vary along a width direction of the film-shape intermediate product or along a direction in which a plurality of the linear-shape intermediate products are arranged.

In this case, an elastic composite sheet can be manufactured in which the coefficient of elasticity of the elastic member varies according to the position in the width direction (a direction vertical to the flow direction and the thickness direction of the elastic composite sheet) of the elastic composite sheet.

In this case, an elastic member that varies in contraction characteristics along the width direction can be obtained.

Moreover, to solve the above-mentioned problem, the present invention provides an elastic composite sheet manufacturing device structured as follows:

The elastic composite sheet manufacturing device is provided with: (a) a discharge mechanism that has a discharge outlet and discharges an elastic resin material having a thermoplastic elastic resin as a main component which elastic resin material is heat-melted to a temperature higher than a temperature region at which the elastic resin material elastically deforms, from the discharge outlet in a film or a linear shape to form a film-shape or a linear-shape intermediate product; (b) a cooling roller that cools the intermediate product to the temperature region at which the elastic resin material elastically deforms, and hardens the intermediate product to form a film-shape or a linear-shape elastic member; (c) a stretch mechanism including a stretch roller that sends the elastic member drawn from the cooling roller, to a downstream side; and (d) a laminating mechanism that laminates the stretched elastic member on the first base material sheet and bonds the elastic member to the first base material sheet. The cooling roller rotates at a circumferential speed higher than a feeding speed of the elastic resin material when the elastic resin material is discharged from the discharge outlet, and extends the intermediate product at a temperature higher than the temperature region at which the elastic resin material elastically deforms, until the thickness or width of the film-shape intermediate product or the thickness of the linear-shape intermediate product assumes a prescribed value. The stretch mechanism is structured so that the stretch roller stretches the elastic member at a prescribed stretching ratio.

According to the above-described structure, an elastic composite sheet having desired characteristics such as desired stretching stress can be easily manufactured, and furthermore, the manufacturing cost can be reduced.

Preferably, the laminating mechanism superposes the second base material sheet on the stretched elastic member and the first base material sheet so that the elastic member is sandwiched between the first base material sheet and the second base material sheet, and bonds the second base material sheet to at least one of the stretched elastic member and the first base material sheet.

In this case, an elastic composite sheet can be manufactured in which the elastic member is sandwiched between the first and second base material sheets.

Preferably, the circumferential speed of the cooling roller periodically changes.

In this case, an elastic composite sheet can be manufactured in which the coefficient of elasticity of the elastic member varies according to the position in the extension direction of the elastic member.

Preferably, the circumferential speed of the stretch roller periodically changes.

In this case, an elastic composite sheet can be manufactured in which the stretching rate of the elastic member varies according to the position in the extension direction of the elastic member.

Preferably, the discharge mechanism forms the film-shape intermediate product or a plurality of the linear-shape intermediate products. On the cooling roller, a condition for cooling the intermediate product varies along an axial direction of the cooling roller.

In this case, an elastic composite sheet can be manufactured in which the coefficient of elasticity of the elastic member varies according to the position in the width direction (a direction vertical to the flow direction and the thickness direction of the elastic composite sheet in the manufacturing process) of the elastic composite sheet.

Effects of the Invention

According to the present invention, an elastic composite sheet having desired characteristics can be easily manufactured, and furthermore, the manufacturing cost can be reduced.

BRIEF DESCRIPTION OF THE DRAWINGS

SECOND EMBODIMENT

MODE FOR CARRYING OUT THE INVENTION

Hereinafter, embodiments of the present invention will be described with reference to the drawings.

<First embodiment> A manufacturing method and manufacturing device of an elastic composite sheet of a first embodiment will be described with reference to FIGS. 1 to 4.

Figure 1:
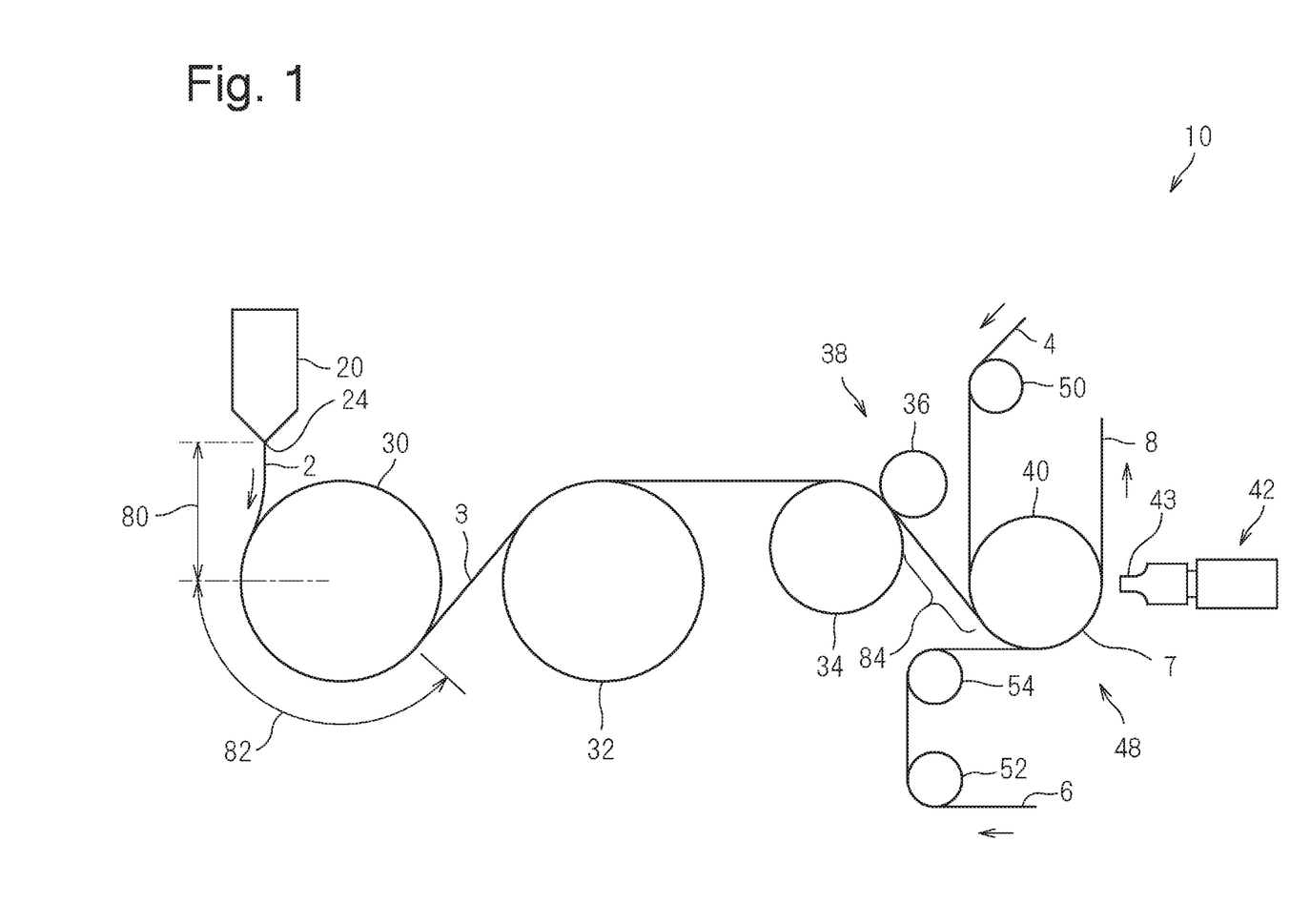
FIG. 1 is a schematic illustration showing the general structure of an elastic composite sheet manufacturing device. (First embodiment).

FIG. 1 is a schematic illustration showing the general structure of an elastic composite sheet manufacturing device 10. As shown in FIG. 1, the elastic composite sheet manufacturing device 10 is provided with a discharge mechanism 20, a cooling roller 30, a stretch mechanism 38, a laminating mechanism 48, and a non-illustrated control device. The control device controls the discharge mechanism 20, the cooling roller 30, the stretch mechanism 38 and the laminating mechanism 48 so as to operate in cooperation with one another.

The discharge mechanism 20 discharges a heat-melted elastic resin material in a film or a linear shape to form a film-shape or a linear-shape intermediate product 2. The elastic resin material has a thermoplastic elastic resin as the main component, and is heat-melted to a temperature higher than a temperature region at which the elastic resin material elastically deforms.

Figure 2A:
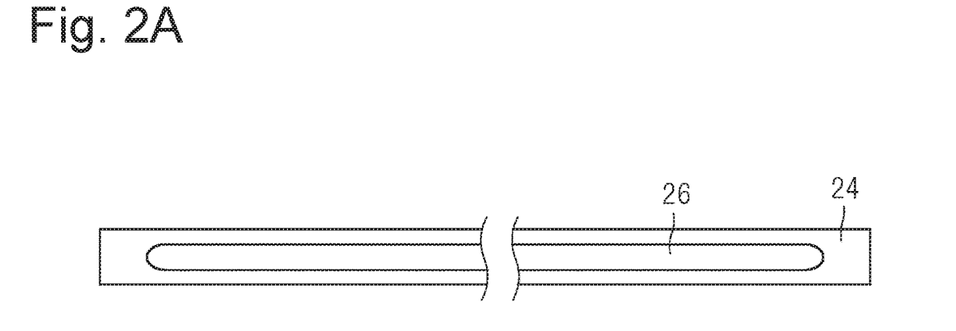
FIGS. 2(a) and 2(b) are schematic illustrations of a bottom surface of a discharge mechanism. (First embodiment).
Figure 2B:
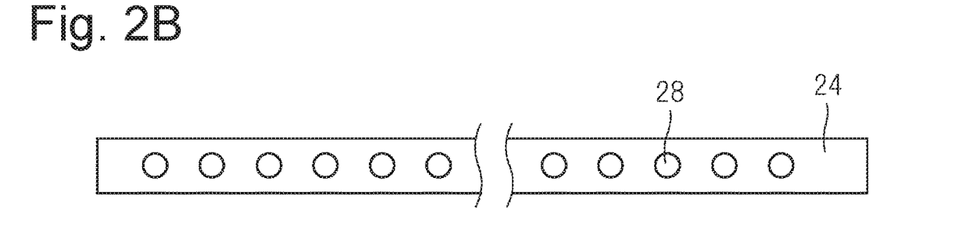

FIGS. 2(a) and 2(b) are schematic illustrations of a bottom surface 24 of the discharge mechanism 20. As shown in FIGS. 2(a) and 2(b), the discharge mechanism 20 has a discharge outlet 26 or 28 that discharges the heat-melted elastic resin material. When the discharge mechanism 20 has the slit-like discharge outlet 26 as shown in FIG. 2(a), the heat-melted elastic resin material is discharged in a film shape to form a film-shape intermediate product 2. When the discharge mechanism 20 has a plurality of discharge outlets 28 as shown in FIG. 2(b), the heat-melted elastic resin material is discharged in a linear shape to form a plurality of intermediate products 2. The discharge mechanism 20 may have only one discharge outlet 28 to form only one linear-shape intermediate product 2.

As shown in FIG. 1, the cooling roller 30 is disposed below the discharge mechanism 20, and the intermediate product 2 discharged from the discharge mechanism 20 is extended in a first section 80 to when it reaches the cooling roller 30. That is, the cooling roller 30 rotates at a circumferential speed higher than the feeding speed of the elastic resin material when it is discharged from the discharge outlet of the discharge mechanism 20, and extends the intermediate product 2 until the thickness of the film-shape intermediate product 2 or the thickness of the linear-shape intermediate product 2 assumes a prescribed value.

In the cooling roller 30, a non-illustrated flow path where a coolant flows is formed, and in a second section 82 in which the intermediate product 2 is in contact with the outer peripheral surface of the cooling roller 30, the cooling roller 30 cools the intermediate product 2 to the temperature region at which the elastic resin material forming the intermediate product 2 elastically deforms, and hardens it. Thereby, the intermediate product 2 becomes a film-shape or linear-shape elastic member 3 in the second section 82, and is drawn from the cooling roller 30.

The elastic member 3 is sent to the stretch mechanism 38 by way of a guide roller 32. The guide roller 32 may be provided with a cooling function. The stretch mechanism 38 includes a drawing roller 34, a pinch roller 36 and a stretch roller 40. The elastic member 3 is sandwiched between the drawing roller 34 and the pinch roller 36 so as not to slide along the outer peripheral surface of the drawing roller 34. The rotation of the drawing roller 34 synchronizes with the rotation of the cooling roller 30.

The elastic member 3 is stretched in a third section 84 from when it is between the drawing roller 34 and the pinch roller 36 to when it reaches the stretch roller 40. That is, the stretch roller 40 rotates at a circumferential speed higher than that of the drawing roller 34 to stretch the elastic member 3 at a prescribed stretching ratio. The elastic member 3 being stretched is along the outer peripheral surface of the stretch roller 40.

The laminating mechanism 48 supplies continuous first nonwoven fabric 4 as a first base material sheet to the stretch roller 40 through a guide roller 50, and supplies continuous second nonwoven fabric 6 as a second base material sheet to the stretch roller 40 through guide rollers 52 and 54. The elastic member 3 stretched along the stretch roller 40 is sandwiched between the first nonwoven fabric 4 and the second nonwoven fabric 6, so that a laminated body 7 in which the elastic member 3, the first nonwoven fabric 4 and the second nonwoven fabric 6 are laminated is formed.

The laminated body 7 moves with the rotation of the stretch roller 40, and passes between the stretch roller 40 and a horn 43 of an ultrasonic bonding device 42. The horn 43 comes into contact with and separates from the stretch roller 40 and when the laminated body 7 is sandwiched between the stretch roller 40 and the horn 43, the elastic member 3 and the first and second nonwoven fabrics 4 and 6 are supersonically bonded. Thereby, an elastic composite sheet 8 in which the elastic member 3 and the first and second nonwoven fabrics 4 and 6 are intermittently bonded is formed and drawn from the laminating mechanism 48. Regarding the first and second nonwoven fabrics 4 and 6, parts thereof directly opposing without the elastic member 3 in between may be supersonically bonded together.

Specifically, the stretch roller 40 has, on its outer peripheral surface, a plurality of non-illustrated protrusions formed at intervals from one another, and functions as an anvil. Of the laminated body 7, the parts sandwiched between the protrusions of the stretch roller 40 and the horn 43 are supersonically bonded. By the supersonic bonding, desired parts can be easily and accurately bonded.

Instead of supersonic bonding, the elastic member 3 and the first and second nonwoven fabrics 4 and 6 of the laminated body 7 may be heat-welded by heat sealing or the like, or the elastic member 3 and the first and second nonwoven fabrics 4 and 6 of the laminated body 7 may be bonded by using an adhesive agent.

Moreover, the elastic member 3 may be held between the first nonwoven fabric 4 and the second nonwoven fabric 6 only by the friction between the first nonwoven fabric 4 and the second nonwoven fabric 6 without being bonded to the first nonwoven fabric 4 or the second nonwoven fabric 6. For example, the first and second nonwoven fabrics 4 and 6 are bonded together at an interval smaller than the width of the elastic member 3 in a relaxed state on both sides in the width direction of the elastic member 3 in a stretched state; then, the stretched state of the elastic member 3 is released, and the elastic member 3 having become thick because of the relaxing is sandwiched between the bonded parts of the first and second nonwoven fabrics 4 and 6 so that the elastic member 3 is brought into a state of being held between the first and second nonwoven fabrics 4 and 6 by the frictional force caused between the elastic member 3 and the first and second nonwoven fabrics 4 and 6.

Two or more bonding modes may be combined.

The stretch roller 40 serves both as the stretch mechanism 38 and the laminating mechanism 48. While this simplifies the structure of the elastic composite sheet manufacturing device 10, a structure provided with separate rollers as the stretch mechanism 38 and the laminating mechanism 48 may be adopted.

Figure 3A:
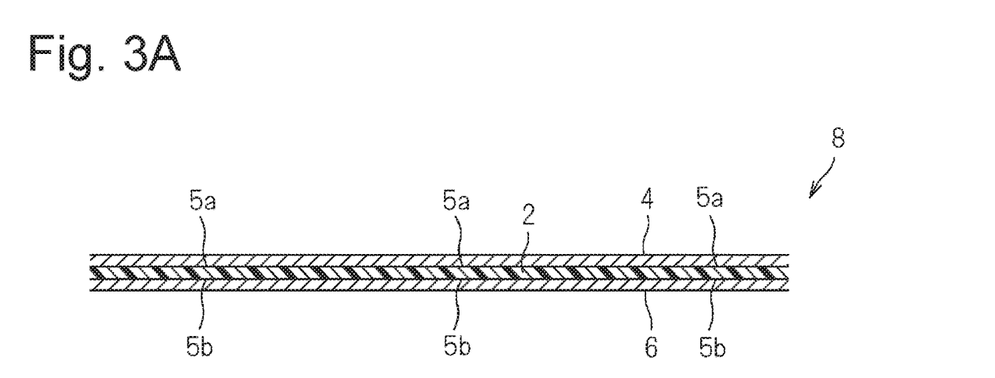
FIG. 3(a) is a cross-sectional view of an elastic composite sheet when an elastic member is in a stretched state.

FIG. 3(a) is a cross-sectional view of the elastic composite sheet 8 when the elastic member 3 is in a stretched state. As shown in FIG. 3(a), the elastic member 3 and the first and second nonwoven fabrics 4 and 6 are intermittently bonded at bonded parts 5a and 5b.

Figure 3B:
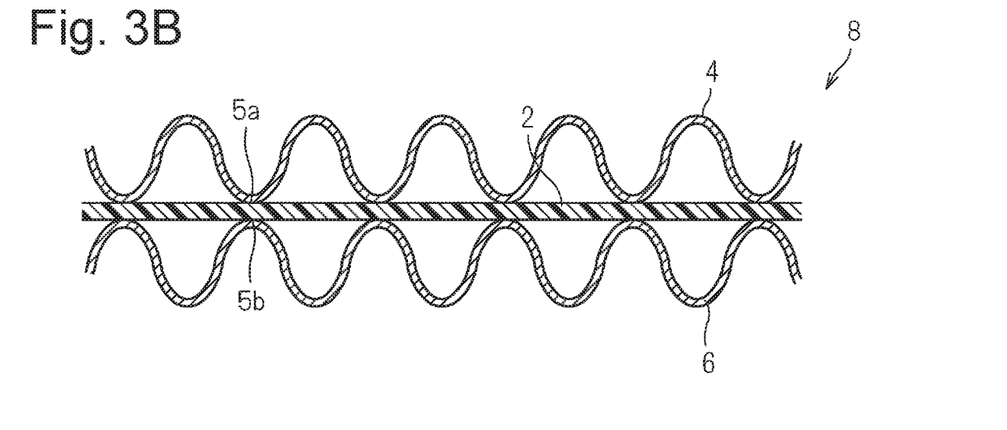
FIG. 3(b) is a cross-sectional view of the elastic composite sheet when the stretched state is released. (First embodiment).

FIG. 3(b) is a cross-sectional view of the elastic composite sheet when the stretched state is released. As shown in FIG. 3(b), when the stretched state of the elastic member 3 is released, the distance between the bonded parts 5a and 5b is reduced, so that the first and second nonwoven fabrics 4 and 6 are curved to form projections and depressions on the surface.

Figure 4A:
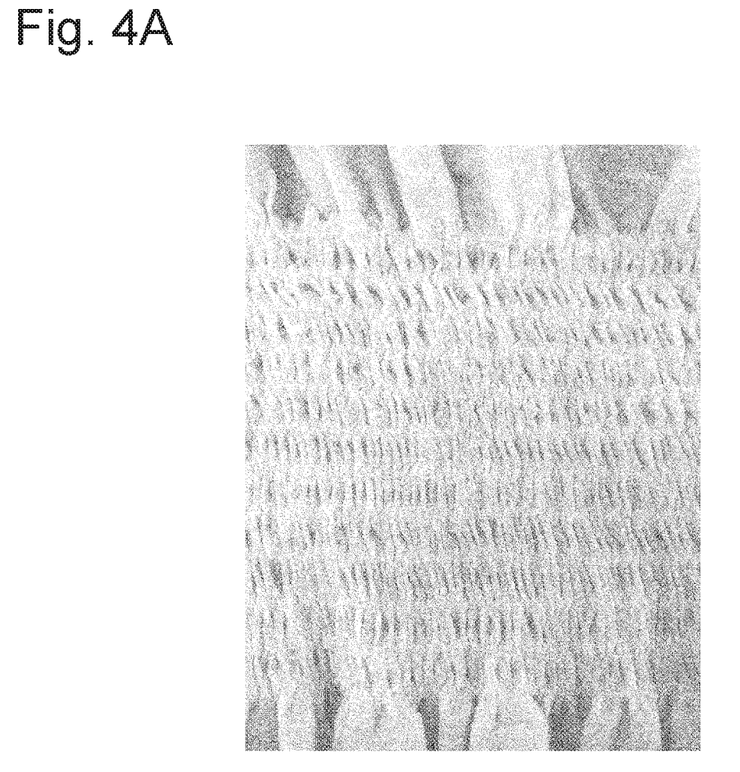
FIGS. 4(a) and 4(b) show pictures of a production example of the elastic composite sheet. (First embodiment).
Figure 4B:
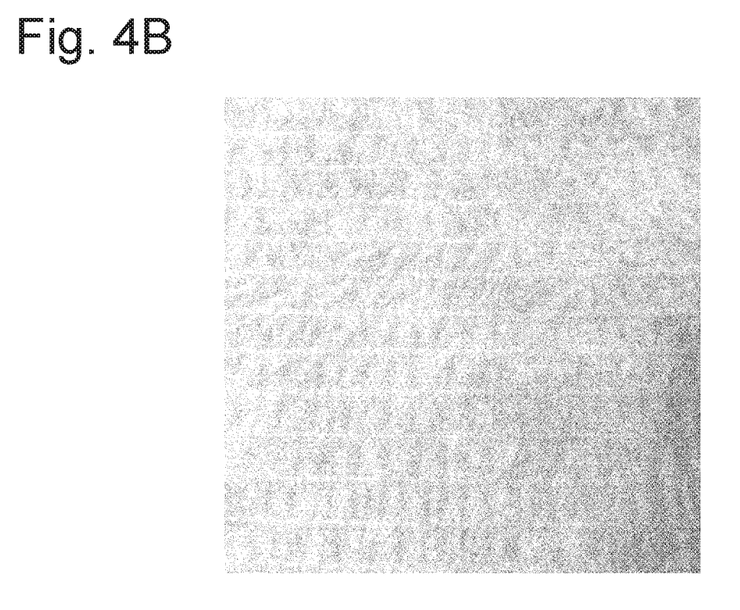

FIGS. 4(a) and 4(b) show pictures of a production example of the elastic composite sheet. FIG. 4(a) shows a natural state in which gathers are formed on the surface of the elastic composite sheet. FIG. (b) shows a state in which the elastic composite sheet is stretched. From FIG. 4(b), it is seen that a plurality of elastic members are stretched in the horizontal direction so that the gathers on the nonwoven fabric surface are gone and the nonwoven fabrics are bonded in a dotted pattern at parts not overlapping with the elastic member.

It is desirable that the thermoplastic elastic resin as the material of the elastic member 3 be a thermoplastic resin that exhibits rubber elasticity at room temperature; for example, an appropriate kind may be selected from among thermoplastic elastomers defined and classified in JIS K 6418:2007 (ISO 18064:2003). For example, a thermoplastic elastomer that elastically deforms in a temperature region of not more than approximately 100 degrees C. is used.

Specific examples include an olefinic elastomer such as "VERSIFY" (trademark) of The Dow Chemical Company, a propylene elastomer such as "Vistamaxx" (trademark) of Exxon Mobil Corporation, and a styrene elastomer such as "Quintac" (trademark) of Zeon Corporation.

The elastic composite sheet manufacturing device 10 is capable of easily manufacturing the elastic composite sheet 8 having desired characteristics. Moreover, the process of manufacturing the elastic member 3 from the elastic resin material that has a thermoplastic elastic resin as the main component and laminating it on the nonwoven fabrics 4 and 6 to complete the elastic composite sheet 8 can be continuously performed and it is unnecessary to prepare a preprocessed elastic member 3, so that the manufacturing cost can be reduced.

The extension rate of the intermediate product 2 in the first section 80 can be adjusted by the feeding speed and discharge amount of the elastic resin material when it is discharged from the discharge mechanism 20 and the circumferential speed (the outside diameter, the number of rotations) of the cooling roller 30. By periodically changing the extension rate of the intermediate product 2, an elastic composite sheet can be manufactured in which the coefficient of elasticity of the elastic member 3 varies according to the position in the extension direction of the elastic member 3.

The stretching rate of the elastic member 3 in the third section 84 can be adjusted by changing the difference in circumferential speed between the drawing roller 34 and the stretch roller 40. By periodically changing the circumferential speed of the stretch roller 40 and periodically changing the stretching rate of the elastic member 3 in the third section 84, an elastic composite sheet can be manufactured in which the stretching rate of the elastic member 3 varies according to the position in the stretching direction of the elastic member 3.

When the discharge mechanism 20 forms the film-shape intermediate product 2 or a plurality of the linear-shape intermediate products 2, the conditions for cooling the intermediate product 2 such as the surface temperature and the thermal conductivity may be varied in the axial direction of the cooling roller 30. In this case, the elastic composite sheet 8 can be manufactured in which the coefficient of elasticity of the elastic member 3 varies according to the position in the width direction (a direction vertical to the flow direction and the thickness direction of the elastic composite sheet 8 in the manufacturing process) of the elastic composite sheet 8.

When the elastic composite sheet 8 includes a plurality of linear-shape elastic members 3, characteristics such as the position of disposition, the coefficient of elasticity and the stretching rate can be adjusted for each elastic member 3 according to the shape, number and disposition of the discharge outlet of the discharge mechanism 20.

Next, referring to FIG. 1, the manufacturing method of the elastic composite sheet 8 will be described. First, the elastic resin material having a thermoplastic elastic resin as the main component is heated and melted (first step). Then, the melted elastic resin material is discharged in a film or linear shape to form a film-shape or a linear-shape intermediate product 2 (second step). Then, at a temperature higher than the temperature region at which the elastic resin material elastically deforms, the intermediate product 2 is extended until the thickness or width of the film-shape intermediate product or the thickness of the linear-shape intermediate product assumes a prescribed value (third step). Then, the intermediate product 2 is cooled to the temperature region at which the elastic resin material elastically deforms, and is hardened to form a film-shape or linear-shape elastic member 3 (fourth step). Then, the elastic member 3 is stretched to a prescribed stretching ratio (fifth step). Then, the stretched elastic member 3 is laminated on and bonded to the first nonwoven fabric 4 (sixth step). At the sixth step, the second nonwoven fabric 6 is superposed on the elastic member 3 and the first nonwoven fabric 4 in such a manner that the elastic member 3 is sandwiched between the first nonwoven fabric 4 and the second nonwoven fabric 6, and (a) the second nonwoven fabric 6 is bonded to at least one of the stretched elastic member 3 and the first nonwoven fabric 4 or (b) the second nonwoven fabric 6 is bonded to the first nonwoven fabric 4, the elastic member 3 is not bonded to the first nonwoven fabric 4 or the second nonwoven fabric 6 and only by the friction between the first nonwoven fabric 4 and the second nonwoven fabric 6, the elastic member 3 is held between the first nonwoven fabric 4 and the second nonwoven fabric 6 (sub step).

<First modification> A structure may be adopted in which the laminating mechanism 48 of the elastic composite sheet manufacturing device 10 supplies, of the first nonwoven fabric 4 and the second nonwoven fabric 6, only the first nonwoven fabric 4 and the elastic member 3 is laminated on and bonded to the first nonwoven fabric 4. In this case, an elastic composite sheet having stretchability can also be manufactured.

In this case, the manufacturing method of the elastic composite sheet does not include the sub step of the manufacturing method of the elastic composite sheet of the first embodiment.

Figure 5:
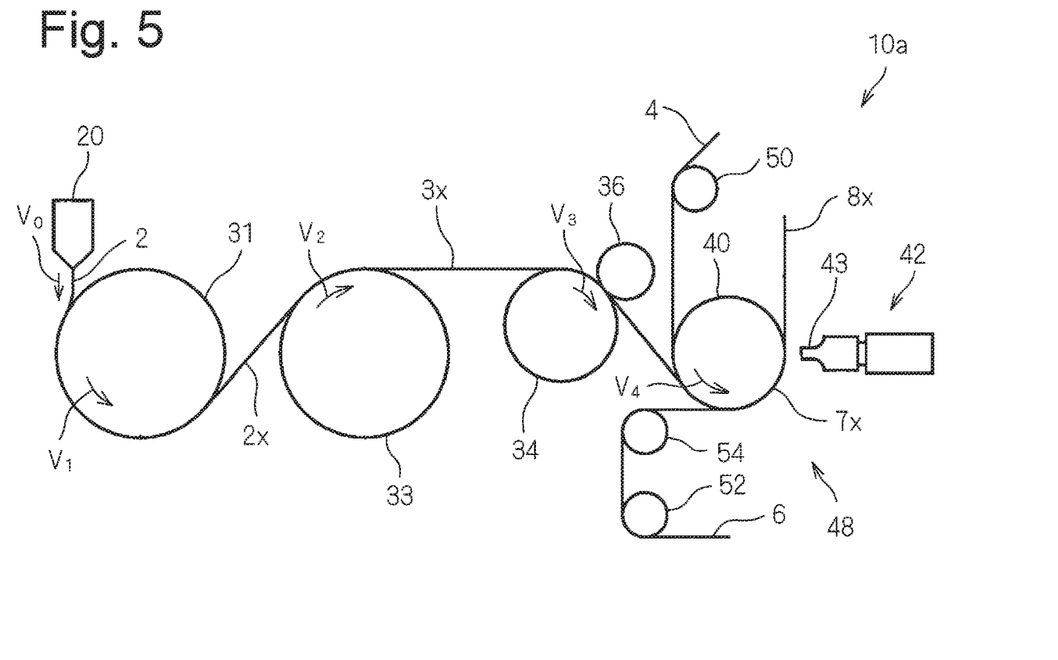
FIG. 5 is a schematic illustration showing the general structure of an elastic composite sheet manufacturing device. (Second embodiment).
Figure 6:
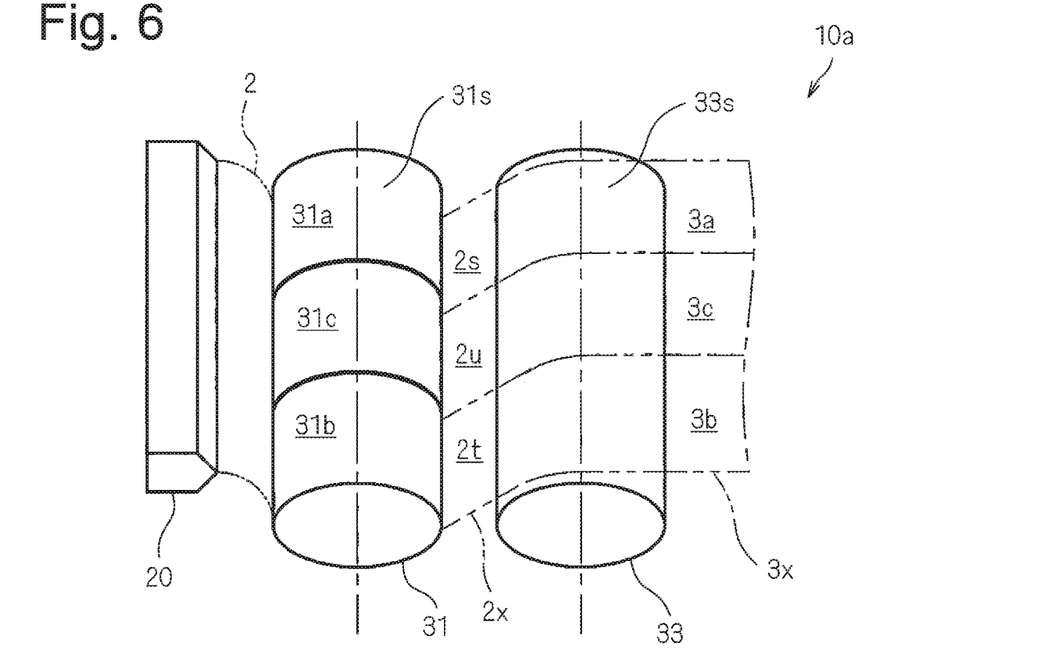
FIG. 6 is a relevant part explanatory view of the elastic composite sheet manufacturing device.

<Second embodiment> A second embodiment will be described with reference to FIGS. 5 and 6. FIG. 5 is a schematic illustration showing the general structure of an elastic composite sheet manufacturing device 10a. FIG. 6 is a relevant part explanatory view of the elastic composite sheet manufacturing device 10a. In the following, the same reference designations are used for the same parts as those of the first embodiment, and differences from the first embodiment will be mainly described.

As shown in FIG. 5, the elastic composite sheet manufacturing device 10a is provided with a first and second cooling rollers 31 and 33 as cooling members instead of the cooling roller 30 and the guide roller 32 of the elastic composite sheet manufacturing device 10 of the first embodiment. As in the first embodiment, the discharge mechanism 20 discharges the heat-melted elastic resin material in a film shape or a linear shape.

As shown in FIG. 6, the first cooling roller 31 is structured so that the temperature condition varies along the axial direction. That is, of the outer peripheral surface 31s of the first cooling roller 31, both end regions 31a and 31b have a temperature within the temperature region at which the elastic resin material (intermediate product 2) discharged from the discharge mechanism 20 elastically deforms, and the central region 31c has a temperature higher than the temperature region at which the elastic resin material (intermediate product 2) elastically deforms.

As shown in FIG. 5, the speed (circumferential speed) $V_1$ of the first cooling roller 31 is made higher than the feeding speed $V_0$ of the elastic resin material when it is discharged from the discharge mechanism 20. Thereby, the intermediate product 2 discharged from the discharge mechanism 20 is extended.

Of the intermediate product 2, the end parts that are in contact with the both end regions 31a and 31b of the outer peripheral surface 31s of the first cooling roller 31 are cooled to the temperature region at which the elastic resin material elastically deforms, and hardened to exhibit elasticity. On the other hand, the central part that is in contact with the central region 31c of the outer peripheral surface 31s of the first cooling roller 31 remains in an extendable state because the temperature thereof is higher than the temperature region at which the elastic resin material elastically deforms.

The second cooling roller 33 is structured so that the entire outer peripheral surface 33s has a temperature within the temperature region at which the elastic resin material elastically deforms. The speed (circumferential speed) $V_2$ of the second cooling roller 33 is made higher than the speed (circumferential speed) $V_1$ of the first cooling roller 31. Thereby, of an intermediate product 2x drawn from the first cooling roller 31, both end parts 2s and 2t having passed the both end regions 31a and 31b of the outer peripheral surface 31s of the first cooling roller 31 are stretched. On the other hand, of the intermediate product 2x drawn from the first cooling roller 31, a central part 2u having passed the central region 31c of the outer peripheral surface 31s of the first cooling roller 31 is extended between the first cooling roller 31 and the second cooling roller 33, and by coming into contact with the second cooling roller 33, the central part 2u is cooled to the temperature region at which the elastic resin material elastically deforms, and hardened to exhibit elasticity.

When discharged from the second cooling roller 33, the intermediate product 2x becomes an elastic member 3x any part in the width direction (a direction vertical to the flow direction and the thickness direction of the intermediate product 2x in the manufacturing process) of which exhibits elasticity.

The speed (circumferential speed) $V_3$ of the drawing roller 34 is made higher than the speed (circumferential speed) $V_2$ of the second cooling roller 33. Thereby, the elastic member 3x drawn from the second cooling roller 33 is stretched both in the both end parts 3a and 3b and in the central part 3c.

The speed (circumferential speed) $V_4$ of the stretch roller 40 is made higher than the speed (circumferential speed) $V_3$ of the drawing roller 34. Thereby, the elastic member 3x drawn from the drawing roller 34 is stretched both in the both end parts 3a and 3b and in the central part 3c.

As in the first embodiment, the elastic member 3x is laminated on the first and second nonwoven fabrics 4 and 6 by the laminating mechanism 48 to form a laminated body 7x. The laminated body 7x is supersonically bonded when passing between the stretch roller 40 and the horn 43 of the ultrasonic bonding device 42, whereby an elastic composite sheet 8x is formed in which the elastic member 3x and the first and second nonwoven fabrics 4 and 6 are intermittently bonded.

The following Table 1 shows combinations of extension and stretching due to the speed differences among $V_1$ to $V_4$ regarding the both end parts 3a and 3b and the central part 3c of the elastic member 3x. Here, $V_0<V_1<V_2<V_3$.

TABLE 1

| $V_0$ | $V_1$ | $V_2$ | $V_3$ |
|---|---|---|---|
| Both ends | Extension | Stretching | Stretching |
| Center | Extension | Extension | Stretching |

For example, the contraction force and the contraction amount in the flow direction of the elastic member 3x prototyped with $V_0:V_1:V_2:V_3=100:150:200:300$ are shown in the following Table 2. Compared with the central part 3c, the both end parts 3a and 3b of the elastic member 3x are high in contraction force and largely contract.

TABLE 2

| | Contraction force | Contraction amount |
|---|---|---|
| Both ends | 66% | 50% |
| Center | 50% | 66% |

That is, the elastic resin material extruded in the center in the width direction does not exhibit elasticity at the first cooling roller 31, and until coming into contact with the second cooling roller 33 on the downstream side, the elastic resin material is extended so that the thickness or the width is further reduced, whereby a region having a less contraction stress than the both end parts can be formed.

By providing a plurality of cooling members (first and second cooling rollers 31 and 33) having different temperature conditions so that the intermediate products 2 and 2x of the heat-melted and discharged elastic resin material pass the plurality of cooling members (first and second cooling rollers 31 and 33) successively and cooling the intermediate products 2 and 2x in a plurality of steps, the elastic member 3x that varies in contraction characteristics along the width direction can be obtained. Moreover, it is easy to stabilize the quality of the elastic member 3x.

The cooling member may have a shape other than the roller shape, such as an endless belt shape. Three or more cooling members may be used.

Figure 7:
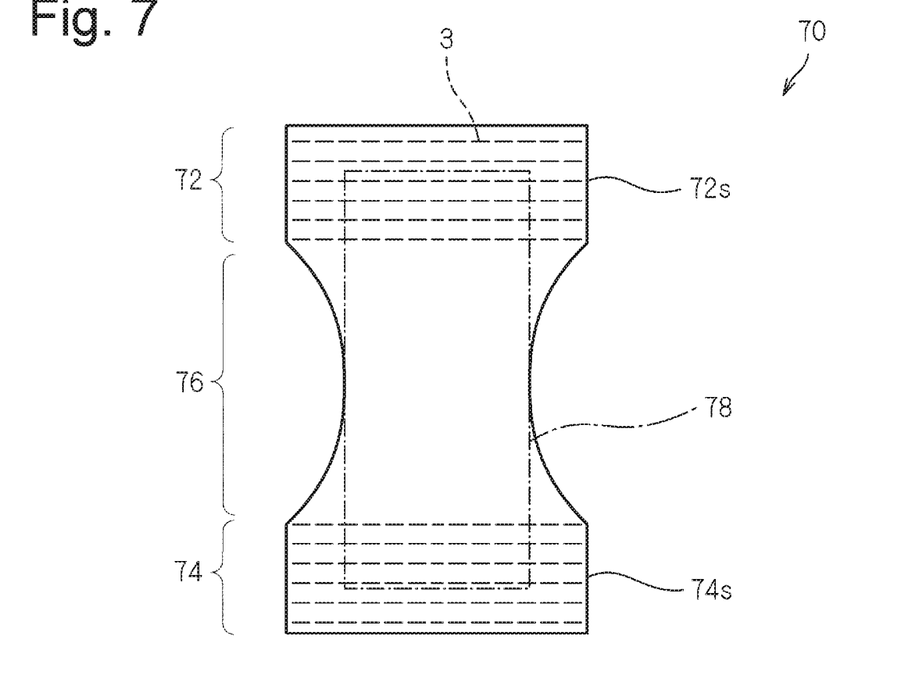
FIG. 7 is a schematic illustration of a disposable wearing article. (Third embodiment)

<Third embodiment> A disposable wearing article 70 using the elastic composite sheet 8 or 8x manufactured according to the first embodiment or the second embodiment will be described with reference to FIG. 7. FIG. 7 is a schematic illustration of the disposable wearing article 70.

As shown in FIG. 7, in the disposable wearing article 70, a front body portion 72 and a rear body portion 74 are opposed at an interval, and a crotch portion 76 is connected to the front body portion 72 and to the rear body portion 74. An absorbent article 78 is disposed so as to lie astride the crotch portion 76. When used, the disposable wearing article 70 is folded at the crotch portion 76, the front body portion 72 is disposed on the ventral side, the rear body portion 74 is disposed on the back side, and the front body portion 72 and the rear body portion 74 are joined by a fastening member such as non-illustrated tape.

In the case of a so-called shorts-type disposable wearing article, a pair of sides 72s of the front body portion 72 and a pair of sides 74s of the rear body portion 74 are previously bonded by heat sealing or the like.

The elastic composite sheet 8 of the first embodiment can be used so that the elastic member 3 is disposed on the front body portion 72 and the rear body portion 74 of the disposable wearing article 70. In this case, it is easy to provide desired characteristics such as the stretching stress and the stretching rate according to the part where the elastic member 3 is used.

The elastic composite sheet of the first embodiment including the film-shape elastic member may be used for the disposable wearing article. In this case, it is also easy to provide desired characteristics such as desired stretching stress and stretching rate according to the part where the film-shape elastic member is used.

The elastic composite sheet 8x of the second embodiment is used, for example, so that the both end parts are disposed in the front body portion 72 and the rear body portion 74 of the disposable wearing article 70 and the central part is disposed in the crotch portion 76 and part of the front body portion 72 and the rear body portion 74. In this case, it is easy to provide desired characteristics such as desired stretching stress and stretching rate in the direction around the body and the direction around the legs.

<Summary> As described above, an elastic composite sheet having desired characteristics can be easily manufactured, and furthermore, the manufacturing cost can be reduced.

The present invention is not limited to the above-described embodiments and may be variously modified when carried out.

For example, while the elastic composite sheet in which the elastic member and the nonwoven fabrics are laminated and bonded is shown as an example, a base material sheet other than a nonwoven fabric may be used to manufacture an elastic composite sheet.

Moreover, two or more discharge mechanisms may be used. In this case, an elastic member may be formed by superposing intermediate products discharged from different discharge mechanisms one on another.

EXPLANATIONS OF LETTERS OR NUMERALS 2, 2x Intermediate product
3, 3x Elastic member
4 First nonwoven fabric (first base material sheet)
6 Second nonwoven fabric (second base material sheet)
8, 8x Elastic composite sheet
10, 10a Elastic composite sheet manufacturing device
20 Discharge mechanism
26, 28 Discharge outlet
30, 31, 33 Cooling roller (cooling member)
38 Stretch mechanism
40 Stretch roller
48 Laminating mechanism

The invention claimed is:

1. An elastic composite sheet manufacturing method comprising:
    a first step of heating and melting an elastic resin material having a thermoplastic elastic resin as a main component;
    a second step of forming a film-shape or a linear-shape intermediate product by discharging the melted elastic resin material in a film or a linear shape;
    a third step of extending the intermediate product at a temperature higher than a temperature region at which the elastic resin material elastically deforms, until a thickness or width of the film-shape intermediate product or a thickness of the linear-shape intermediate product assumes a prescribed value;
    a fourth step of forming a film-shape or a linear-shape elastic member by contacting the intermediate product with a cooling member, so as to cool the intermediate product to a temperature region at which the elastic resin material elastically deforms and hardening the intermediate product;
    a fifth step of stretching the elastic member to a prescribed stretching ratio; and
    a sixth step of laminating the stretched elastic member on a first base material sheet and bonding the elastic member to the first base material sheet,
    wherein at the third and fourth steps, by providing a plurality of cooling members having different temperature conditions so that the intermediate product passes the cooling members successively, the intermediate product is cooled in a plurality of steps, and
    wherein at the third and fourth steps, a condition for cooling the intermediate product is made to vary along a width direction of the film-shape intermediate product or along a direction in which a plurality of the linear-shape intermediate products are arranged.

2. The elastic composite sheet manufacturing method according to claim 1, wherein at the sixth step, a second base material sheet is superposed on the elastic member and the first base material sheet in such a manner that the elastic member is sandwiched between the first base material sheet and the second base material sheet,
    the second base material sheet is bonded to at least one of the stretched elastic member and the first base material sheet, or
    the second base material sheet is bonded to the first base material sheet, the elastic member is not bonded to the first base material sheet or the second base material sheet and only by friction between the first base material sheet and the second base material sheet, the elastic member is held between the first base material sheet and the second base material sheet.

3. The elastic composite sheet manufacturing method according to claim 1, wherein at the third step, the intermediate product is extended by periodically changing the prescribed value to which the intermediate product is extended.

4. The elastic composite sheet manufacturing method according to claim 1, wherein at the fifth step, the elastic member is stretched while the prescribed stretching ratio to which the elastic member is stretched is periodically changed.

5. The elastic composite sheet manufacturing method according to claim 1, further comprising, after bonding the stretched elastic member to the first base material sheet, releasing a stretched state so that the first base material sheet is curved to form projections and depressions.

6. The elastic composite sheet manufacturing method according to claim 1, wherein in the fourth step, the intermediate product after the third step contacts lateral and lower sides of the cooling member to cool the intermediate product.

* * * * *